Figure 1:
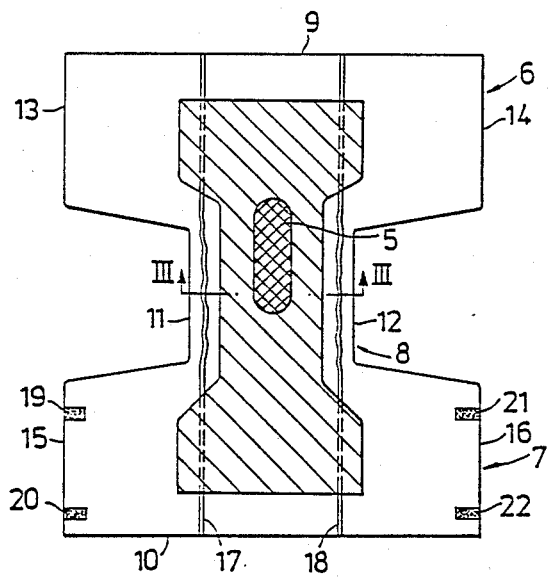

United States Patent [19]

Singheimer

[11] Patent Number: 4,854,989
[45] Date of Patent: Aug. 8, 1989

[54] METHOD OF AFIXING ELASTIC BANDS IN AN INCONTINENCE DIAPER

[75] Inventor: Stig A. R. Singheimer, Halmstad, Sweden

[73] Assignee: Duni Bila AB, Sweden

[21] Appl. No.: 73,761

[22] Filed: Jul. 15, 1987

Related U.S. Application Data

[62] Division of Ser. No. 881,684, filed as PCT SE84/00356 on Oct. 24, 1984, published as WO8602530 on May 9, 1986, Pat. No. 4,718,901.

[30] Foreign Application Priority Data

Oct. 24, 1984 [WO] PCT Int'l
 Appl. .................... PCT/SE84/00356

[51] Int. Cl.$^4$ ............................................. B65H 77/00
[52] U.S. Cl. ..................................... 156/161; 156/229
[58] Field of Search ............... 156/164, 229, 495, 163, 156/494, 161, 176, 177, 178, 179, 299, 302, 303; 604/385.1, 385.2; 112/121.26

[56] References Cited

U.S. PATENT DOCUMENTS

| | | | |
|---|---|---|---|
| 2,681,020 | 6/1954 | Liebowitz et al. | 112/121.26 |
| 4,239,578 | 12/1980 | Gore | 156/164 X |
| 4,309,236 | 1/1982 | Teed | 156/164 |
| 4,371,417 | 2/1983 | Frick et al. | 156/164 |
| 4,405,397 | 9/1983 | Teed | 156/164 |
| 4,418,123 | 11/1983 | Bunnelle et al. | 156/164 |
| 4,464,217 | 8/1984 | Dickover et al. | 156/495 X |
| 4,543,099 | 9/1985 | Bunnelle et al. | 156/164 |
| 4,556,596 | 12/1985 | Meuli | 156/164 |
| 4,634,482 | 1/1987 | Lammars | 156/164 |

FOREIGN PATENT DOCUMENTS 1186288 4/1985 Canada .................. 156/164

Primary Examiner—Michael W. Ball
Assistant Examiner—David W. Herb
Attorney, Agent, or Firm—Ostrolenk, Faber, Gerb & Soffen

[57] ABSTRACT

The present invention relates to method making an incontinence diaper built up from a barrier layer (1) and a nonwoven layer (2) affixed thereto for providing two portions (6, 7) surrounding the lower part of the body and a crotch portion (8) connecting these portions. At least one elastic band (17, 18) extends from the central part of the crotch portion (8) along both side edges (11, 12) of said portion, in over both portions (6, 7) and along the entire length of the diaper with the elastic band (17, 18) being attached with a continuously varying tension in the diaper material. The tension in the elastic band (17, 18) is greatest at the crotch portion (8) and dimishes to approximately half it value over both the portions (6, 7).

2 Claims, 2 Drawing Sheets

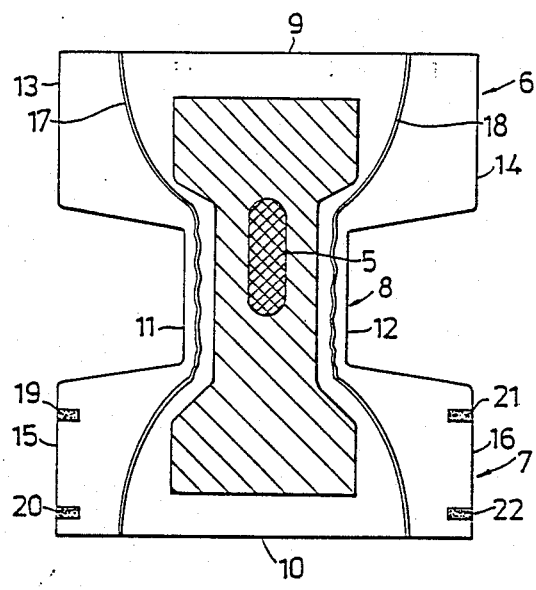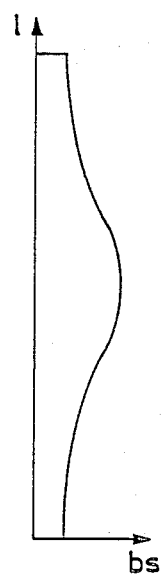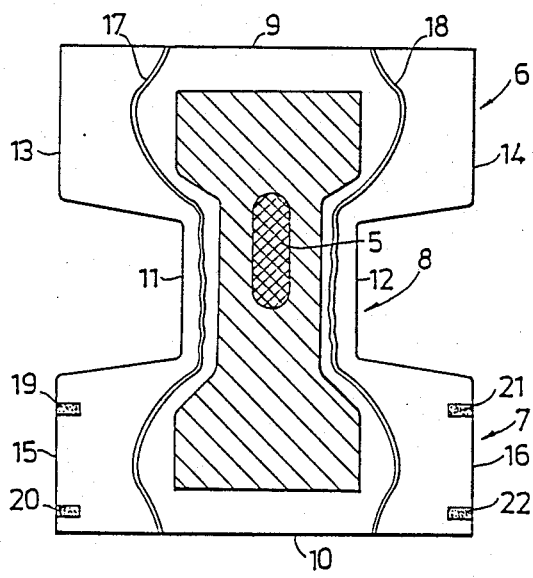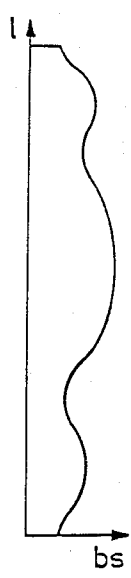

METHOD OF AFIXING ELASTIC BANDS IN AN INCONTINENCE DIAPER

This is a division of application Ser. No. 881,684, filed as PCT SE84/00356 on Oct. 24, 1984, published as WO86/02530 on May 9, 1986, now U.S. Pat. No. 4,718,901.

The present invention relates to an incontinence diaper, comprising a barrier layer of such as polyethylene film with a nonwoven layer fixed to it, and including two portions surrounding the lower part of the body and a crotch portion, connecting these two portions, intended for placing between the legs of a patient or wearer, there extending an area with fluff surrounded by soft tissue in the longitudinal direction of the diaper, over a large part of the portions surrounding the body and nearly the entire width of the crotch portion between the barrier layer and the nonwoven layer, as well at least one elastic band along both opposing sides of the crotch portion outside the fluff for pulling together the crotch portion about the thighs of the wearer when the diaper is in use.

One of the great problems, inter alia, in the care of incontinent patients in medical care is the frequency of leakage in the use of diapers. It has been found that the capillary forces in the absorption body in the diaper cannot counteract gravitation forces to any great extent, and thus there are often leakages, particularly when the patient is lying on his side. The incontinence diapers provided with elastic bands which are on the market today have an extension of the band solely in the crotch portion, and thus optimum flexibility in the whole diaper is not achieved, which means that the diapers must be manufactured in several different sizes, and in spite of this they often leak when in use.

The object of the present invention is to provide an incontinence diaper of the type mentioned in the introduction, in which the drawbacks attached to known diapers have been eliminated. Essentially distinguishing for the invention is that the elastic band continues from the crotch area in over both body-surrounding portions and along the entire length of the diaper with the band being attached with varying tension to the diaper material, this tension being greatest at the central portion of the crotch area, from which the tension decreases somewhat towards the distant portions of this area right up to both body-surrounding portions after which the tension tapers off to about half the original tension at the central portion of the crotch area, for optionally increasing again at the area just before the end eges of the body-surrounding portions to a value close to that at the central portion of the crotch area, for subsequently returning to approximately half of the original tension at the end edges.

With the aid of the invention there is now provided an incontinence diaper with an elastic band which achieves complete moisture-proofing between the body of a patient or wearer and the barrier layer of the diaper, both at the crotch portion of the wearer and around the waist and hips of this person. By the bands being attached with varying tension along substantially the entire diaper and the position of the bands being varied laterally at the waist fastening of the diaper it will be adjustable to patients having different waist measurements and body shapes. Since the bands also have a certain amount of stretch above the crotch area, a comfortable diaper is afforded and there is no risk that the barrier layer of the diaper, which is usually polyethylene film, being stretched out and thereby leaving gaps with leakage as a result. The more the attachment of the band varies transversely in the waist portion, the more will be the above-mentioned effect. Furthermore, the diaper in accordance with the present invention may be used with the same diaper dimension by persons of different sex, different waist measurement and different pelvic length due to the varying band tension.

Figure 2:
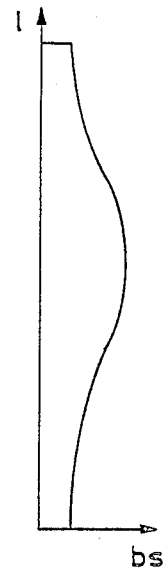
Figure 3:
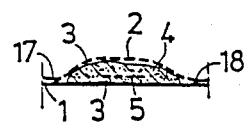

The invention will now be described in detail below with reference to the accompanying drawings, on which FIG. 1 is a plan view of an incontinence diaper in accordance with the present invention, FIG. 2 is a tension diagram for the band tension in the elastic bands illustrated in FIG. 1, FIG. 3 is a section along the line III in FIG. 1, FIG. 4 is a plan view of another embodiment of an incontinence diaper in accordance with the present invention, FIG. 5 is a tension diagram for the band tension in the elastic bands illustrated in FIG. 4, FIG. 6 is a plan view of a third embodiment of the incontinence diaper in accordance with the present invention and FIG. 7 is a tension diagram for the band tension in the elastic bands illustrated in FIG. 6.

As will be seen from FIGS. 1 and 3 the incontinence diaper in accordance with the present invention is made up from a barrier layer 1 of such as polyethylene film, a nonwoven layer 2 fixed to it, and fluff 4 surrounded by a soft tissue material 3 between the layers 1 and 2. The fluff 4 may also have a centrally situated super-absorbent portion 5. The diaper is made with two body-surrounding portions 6 and 7 with a crotch portion 8 connecting these two. The diaper is longitudinally defined by two end edges 9 and 10. The crotch portion 8 has two side edges 11 and 12 running in the longitudinal direction of the diaper, and both portions 6 and 7 are defined laterally by side edges 13, 14, 15, 16. Two mutually parallel elastic bands 17 and 18 extend substantially over the entire length of the diaper, along side edges 11 and 12 of the crotch portion 8 and over the portions 6 and 7. The bands 17 and 18 are attached to the diaper material, e.g. the barrier layer 1, with a continuously varying tension, which is greatest in the crotch portion 8, see FIG. 2. FIG. 2 illustrates the band tension in the bands 17, 18 illustrated in FIG. 1, tension being denoted by bs and diaper length by 1. As will be seen from FIG. 2, the band tension diminishes to about half its value a short distance after the junction between the crotch portion 8 and the portions 6 and 7. In the embodiment as illustrated in FIG. 1, the elastic bands 17 and 18 extend over the parts of the portions 6 and 7 containing fluff 4.

A second embodiment of the diaper in accordance with the present invention is illustrated in FIG. 4, where the elastic bands 17 and 18 diverge over the portions 6 and 7 towards the end edges 9 and 10 of said portions 6 and 7, and FIG. 5 is a tension diagram for the elastic bands 17 and 18 illustrated in FIG. 4.

A third embodiment of a diaper in accordance with the present invention is illustrated in FIG. 6, where the elastic bands 17 and 18 over the portions 6 and 7 diverge to about half the length of these portions, thereafter to converge towards the end portions 9 and 10. FIG. 7 illustrates how the tension varies in the bands 17 and 18 attached to the diaper according to FIG. 6.

The attachment of the elastic band may be carried out by applying a glue, e.g. a so-called hot-melt glue with a short liquid phase time, continuously on the elastic band which is then pressed against the underlying barrier layer 1 by a roll. The tension in the band is regulated by a curve-controlled tension roller, there being thus obtained a continuously varying tension in response to the curve profile in the longitudinal direction of the diaper. The tension roller may also be guided transversely, a transverse displacement of the band being obtained in the longitudinal direction of the diaper and thus also the effects desired in the central area of the diaper. The elastic band may also comprise an elastic, prefabricated material or an elastic glue bead in which the tension is continuously varied by different extension or contraction of the bead on its application.

The diaper in accordance with the present invention is attached to a patient or wearer by the side edges 13, 15 and 14, 16 or the respective body-surrounding portions 6, 7 being attached to each other with the aid of double-sided adhesive tape, 19, 20 and 21, 22 respectively.

I claim:

1. A method for affixing elastic bands in an incontinence diaper comprising a barrier layer and a nonwoven layer affixed to said barrier layer, said diaper having two wasit portions for together surrounding the lower part of a body and a crotch portion connecting the two waist portions, a tissue covered fluff extending between the barrier layer and the nonwoven layer in the longitudinal direction of the diaper through the entire crotch portion and through parts of said waist portions, the method comprising fastening the bands to the diaper by continuously applying a rapid-drying glue to the bands simultaneously as the bands are stretched with a continuously varying tension and without abrupt changes in tension along the longitudinal direction of the diaper and are pressed under a roll against the barrier layer, wherein the tension of the bands reaches a maximum in the central portion of the crotch area, the tension decreasing toward the edges of the crotch area up to the edges of the waist portions, after which the tension tapers off to about half of said maximum tension, the tension increasing again just before the end edges of the wasit portions to a value close to said maximum tension, the tension subsequently returning at the end edges of the waist portions to a value approximately half of said maximum tension.

2. A method as recited in claim 1, wherein said elastic band comprises an elastic glue bead, the tension of said elastic glue bead being continuously varied without abrupt changes in tension by varying the extension or contraction of said elastic glue bead as it is applied directly to the barrier layer.

* * * * *